(12) United States Patent
Gericke et al.

(10) Patent No.: US 9,333,234 B2
(45) Date of Patent: May 10, 2016

(54) COMBINATION OF SOMATOSTATIN-ANALOGS WITH 11BETA-HYDROXYLASE INHIBITORS

(71) Applicants: Germo Hans Gericke, Fischingen (DE); Herbert Anton Schmid, Neuenburg (DE); Mario Roberto Maldonado Lutomirsky, Basel (CH); Li Li, Bridgewater, NJ (US)

(72) Inventors: Germo Hans Gericke, Fischingen (DE); Herbert Anton Schmid, Neuenburg (DE); Mario Roberto Maldonado Lutomirsky, Basel (CH); Li Li, Bridgewater, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/391,416

(22) PCT Filed: Apr. 10, 2013

(86) PCT No.: PCT/EP2013/057515
§ 371 (c)(1),
(2) Date: Oct. 9, 2014

(87) PCT Pub. No.: WO2013/153129
PCT Pub. Date: Oct. 17, 2013

(65) Prior Publication Data
US 2015/0087588 A1 Mar. 26, 2015

Related U.S. Application Data

(60) Provisional application No. 61/623,117, filed on Apr. 12, 2012.

(51) Int. Cl.
A61K 38/31 (2006.01)
A61P 5/02 (2006.01)
C07K 14/655 (2006.01)
A61K 38/12 (2006.01)
A61K 31/4184 (2006.01)
A61K 31/4188 (2006.01)

(52) U.S. Cl.
CPC ............ *A61K 38/12* (2013.01); *A61K 31/4184* (2013.01); *A61K 31/4188* (2013.01); *A61K 38/31* (2013.01)

(58) Field of Classification Search
CPC .......... A61K 2300/00; A61K 31/4184; A61K 38/31; A61K 31/4188; A61K 38/12
See application file for complete search history.

(56) References Cited

U.S. PATENT DOCUMENTS

| 8,575,160 B2 * | 11/2013 | Sun ...................... C07D 487/04 514/233.2 |
| 8,609,862 B2 * | 12/2013 | Hu ..................... A61K 31/4188 548/302.7 |

FOREIGN PATENT DOCUMENTS

| WO | WO2007/024945 | * 3/2007 | ........... C07D 487/04 |
| WO | WO 2011/088188 A1 | 7/2011 | |

OTHER PUBLICATIONS

Boscaro M. et al., "Treatment of Pituitary-Dependent Cushing's Disease with the Multireceptor Ligand Somatostatin Analog Pasireotide (SOM230) A Multicenter, Phase II Trial", Journal of Clinical Endocrinology & Metabolism. vol. 94, No. 1, pp. 115-122, Jan. 2009.

* cited by examiner

*Primary Examiner* — Marcela M Cordero Garcia
(74) *Attorney, Agent, or Firm* — Michelle Han; Gregory Houghton (57) ABSTRACT

The present invention relates to a combination which comprises (a) a somatostatin analog and (b) a 11beta-hydroxylase inhibitor; each in free form or in the form of a pharmaceutical acceptable salt thereof; the use of such a combination for the preparation of a medicament for the treatment of diseases associated with increased stress hormone levels; a commercial package or product comprising such a combination; and to a method of treatment of a warm-blooded animal, especially a human.

12 Claims, 4 Drawing Sheets

COMBINATION OF SOMATOSTATIN-ANALOGS WITH 11BETA-HYDROXYLASE INHIBITORS

The present invention relates to a combination which comprises (a) a somatostatin analogue and (b) a 11beta-hydroxylase inhibitor; each in free form or in the form of a pharmaceutical acceptable salt thereof; the use of such a combination for the preparation of a medicament for the treatment of diseases associated with increased stress hormone levels; a commercial package or product comprising such a combination; and to a method of treatment of a warm-blooded animal, especially a human.

BACKGROUND OF THE INVENTION

The somatostatin class is a known class of small peptides comprising the naturally occurring somatostatin-14 and analogues having somatostatin related activity, e.g. as disclosed by A. S. Dutta in Small Peptides, Vol. 19, Elsevier (1993). By "somatostatin analogue" as used herein is meant any straight-chain or cyclic polypeptide having a structure based on that of the naturally occurring somatostatin-14 wherein one or more amino acid units have been omitted and/or replaced by one or more other amino radical(s) and/or wherein one or more functional groups have been replaced by one or more other functional groups and/or one or more groups have been replaced by one or several other isosteric groups. In general, the term covers all modified derivatives of the native somatostatin-14 which exhibit a somatostatin related activity, e.g. they bind to at least one of the five somatostatin receptor (SSTR), preferably in the nMolar range. Commonly known somatostatin analogs are octreotide, vapreotide, lanreotide, pasireotide.

Pasireotide, having the chemical structure as follow:

Pasireotide is called cyclo[{4-($NH_2$—$C_2H_4$—NH—CO—O-)Pro}-Phg-DTrp-Lys-Tyr(4-Bzl)-Phe], wherein Phg means —HN—CH($C_6H_5$)—CO— and Bzl means benzyl, in free form, in salt or complex form or in protected form.

Cushing's syndrome is a hormone disorder caused by high levels of cortisol in the blood. This can be caused by taking glucocorticoid drugs, or by tumors that produce cortisol or adrenocorticotropic hormone (ACTH) or CRH. Cushing's disease refers to one specific cause of the syndrome: a tumor (adenoma) in the pituitary gland that produces large amounts of ACTH, which elevates cortisol. It is the most common cause of Cushing's syndrome, responsible for 70% of cases excluding glucocorticoid related cases. The significant decrease of cortisol levels in Cushing's disease patients on pasireotide support its potential use as a targeted treatment for Cushing's disease (Colao et al. *N Engl J Med* 2012; 366:32-42).

Compound A is potent inhibitor of the rate-limiting enzyme 11-beta-hydroxylase, the last step in the synthesis of cortisol. WO 2011/088188 suggests the potential use of compound A in treating a disease or disorder characterised by increased stress hormone levels and/or decreased androgen hormone levels, including the potential use of compound A in treating heart failure, cachexia, acute coronary syndrome, chronic stress syndrome, Cushing's syndrome or metabolic syndrome.

Compound A, also called (R)-4-(6,7-Dihydro-5H-pyrrolo [1,2-c]imidazol-5-yl)-3-fluoro-benzonitrile, has formula (II).

Compound A can be synthesized or produced and characterized by methods as described in WO2007/024945.

SUMMARY OF INVENTION

The present invention is, inter alia, based on the data of a 10-week proof-of-concept clinical trial demonstrating the efficacy of compound A with a satisfactory safety profile in patients with Cushing's disease. Compound A successfully reduced urinary free cortisol (UFC) in all patients, for most patients to the normal range of UFC. However for some patients in the trial the UFC level returned to above upper limit of normal (ULN) two weeks after discontinuation of the drug. Furthermore ACTH level was doubled in half of the patients. Hence the present invention aims at maintenance and improvement of Compound A's effects, particularly on the effect on reduction of cortisol level in general, particularly on Compound A's effect in treating or ameliorating a disease or disorder characterised by increased stress hormone levels, particularly by increased cortisol level, including the potential use of compound A in treating heart failure, cachexia, acute coronary syndrome, chronic stress syndrome, Cushing's syndrome or metabolic syndrome.

Thus in the first aspect the present invention provides a combination (will be referred as Combination of the Invention within this application) of (a) Compound A (R)-4-(6,7-Dihydro-5H-pyrrolo[1,2-c]imidazol-5-yl)-3-fluoro-benzonitrile; and (b) a somatostatin analogue, wherein (a) and (b) are present in each case in free form, complex form or in the form of a pharmaceutically acceptable salt.

In one preferred embodiment, the somatostatin analogue is octreotide, vapreotide, lanreotide, or pasireotide. In one preferred embodiment, the somatostatin analogue is pasireotide or any of its pharmaceutically acceptable salts. Preferred salts are the lactate, aspartate, benzoate, succinate and pamoate including mono- and di-salts, more preferably the aspartate di-salt and the pamoate monosalt. Certain salts of pasireotide forms gel in a aqueous environment, such as salt of aspartate, e.g. mono- or diaspartate, glutamate, e.g. mono- or diglutamate, or succinate, e.g. mono- or disuccinate, lactate, acetate or citrate. In one preferred embodiment, the pasireotide pharmaceutically acceptable salt is pamoate salt.

The preferred salt of Compound A is phosphate salt or nitrogen salt. More preferably it is the dihydrogenphosphate salt. The term "phosphate salt" as used in the present application, refers to the acid addition salt of compound A with phosphoric acid. More particularly, it refers to the dihydrogenphosphate of compound A protonated once, that is, wherein compound A is protonated once and thus each molecule carries a single positive charge, while the counterion is $H_2PO_4^-$).

It is surprising that such combination sustains the cortisol reduction effect of Compound A. Furthermore somatostatin analogue and Compound A synergitize each other's effect leading to higher efficacy, less effective dose needed.

The present invention also pertains to a combination for simultaneous, separate or sequential use, such as a combined preparation, including a non-fixed combination or a pharmaceutical fixed combination. A fixed combination refers to both active ingredients present in one dosage form, e.g. in one tablet or in one capsule. Thus a pharmaceutical fixed combination of the present invention comprises (a) a somatostatin analogue and (b) Compound A, in which (a) and (b) are present in each case in free form or in the form of a pharmaceutically acceptable salt, and optionally at least one pharmaceutically acceptable carrier. Preferably the somatostatin analogue is pasireotide.

Pharmaceutically acceptable carrier includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art.

The term "non-fixed combination", as used herein defines that the combination partners (a) and (b) as defined herein can be dosed independently of each other with distinguished amounts of the combination partners (a) and (b), i.e. simultaneously or at different time points. The term "non-fixed combination", includes "kit of parts". The parts of the kit of parts can then, e.g. be administered simultaneously or chronologically staggered, that is at different time points and with equal or different time intervals for any part of the kit of parts.

Preferably, the time intervals are chosen such that the effect on the treated disease in the combined use of (a) and (b) is larger than the effect which would be obtained by use of only any one of the combination partners (a) and (b). The ratio of the total amounts of the combination partner (a) to the combination partner (b) to be administered in the combined preparation can be varied, e.g. in order to cope with the needs of a patient sub-population to be treated or the needs of the single patient which different needs can be due to age, sex, body weight, etc. of the patients. Preferably, there is at least one beneficial effect, e.g. a mutual enhancing of the effect of the combination partners (a) and (b), in particular a synergism, e.g. a more than additive effect, additional advantageous effects, less side effects, a combined therapeutic effect in a non-effective dosage of one or both of the combination partners (a) and (b), and very preferably a strong synergism of the combination partners (a) and (b).

In one aspect the present invention provides the Combination of the Invention for use in the treatment of disease states characterised by elevated level of stress hormone. The term "stress hormone", as used herein, relates to a hormone which is secreted in response to an unusual exposure to life. The stress response involves the activation of both the sympathetic adrenomedullary system with the secretion of epinephrine and norepinephrine, and the hypothalamic pituitary adrenocortical (HPA) system with the secretion of cortisol. In a preferred embodiment, a stress hormone is aldosterone or cortisol, preferably cortisol.

In one preferred embodiment, the present invention provides the Combination of the Invention for use in the treatment of disease characterized by elevated level of cortisol. The term "elevated level of cortisol" as used here refers to the level of cortisol higher than an individual's own normal range of cortisol. The normal range of UFC for population is 10-100 micrograms per 24 hours (mcg/24 h or µg/24 h). Thus the term "elevated level of cortisol" could be defined as higher than 30 µg/24 h, higher than 50 µg/24 h, higher than 70 µg/24 h, higher than 85 µg/24 h or higher than 100 µg/24 h. The term "elevated level of cortisol" could be further defined as higher than 125 µg/24 h, higher than 125 µg/24 h or higher than 200 µg/24 h. The urinary free cortisol (UFC) is measured as a mean 24-hour urinary free cortisol, calculated from four 24-hour samples collected within 2 weeks.

Preferably the term "elevated level of cortisol" refers to a level higher than 80 µg/24 h, higher than 100 µg/24 h or higher than 120 µg/24 h or higher than 150 µg/24 h.

Diseases characterised by elevated level of cortisol includes but is not limited to chronic heart failure, chronic heart failure with impaired exercise tolerance, chronic heart failure with muscle weakness, cardiac cachexia, COPD-induced cachexia, cirrhosis-induced cachexia, tumor-induced cachexia, viral (HIV)-induced cachexia, acute heart failure, acute decompensated heart failure, acute coronary syndrome, chronic stress syndrome, Cushing's syndrome, metabolic syndrome and hypercortisolemia.

Chronic heart failure as well as chronic heart failure conditions with impaired exercise tolerance and muscle weakness show raised plasma aldosterone levels as shown by Bolger et al. Circulation 2002; 106:92-99, a raised plasma to dihydroepiandrosterone ratio as shown by Anker et al. European Heart Journal 1999; 20:683-693 and decreased androgen levels as shown by Jankowaska et al., Circulation 2006; 114:1829-1837.

Cardiac cachexia is a serious complication of chronic heart failure as patients suffer from a general loss of fat tissue, lean tissue and bone tissue. Cardiac cachexia patients show raised plasma levels of aldosterone and cortisol as well as reduced levels of dehydroepiandrosterone as described by Anker et al., Circulation 1997; 96:526-534.

COPD-induced cachexia, cirrhosis-induced cachexia, tumor-induced cachexia and viral (HIV)-induced cachexia are characterized by increased plasma aldosterone levels as documented in WO 2000/21509 or US 2009/0023639 and have been treated with anabolic androgen or androgen-derivatives as reported by Yeh et al., Chest 2002; 122:421-428 and by Cuerda et al., Nutrition Clinical Practice 2005 20; 93-97.

Myocardial infarction raises cortisol levels that affect cardiac remodeling as indicated by Mihailidu et al., Hypertension 2009 in press. The magnitude of the cortisol response is related to the size of the ensuing infarction as shown by Bain et al., International Journal of Cardiology 1992; 27:145-150.

Chronic stress disorders with its physical and psychological ramifications has been associated with excessive aldosterone and cortisol levels according to Kubzansky and Adler, Neuroscience and Biobehavioral Reviews, 2009; 5:1-7. Particularly, excessive and persistent cortisol secretion can lead to depression, hyperglycemia and the suppression of the immune system.

Cushing's syndrome describes a condition of chronically excessive cortisol release. The cortisol excess may originate directly from an adrenocortical tumor or secondarily from a pituitary (Cushing's Disease) or ectopic tumor that releases adrenocorticotropin as illustrated by Boscaro and Arnaldi, Journal of Clinical Endocrinology and Metabolism 2009; 94:3121-3131.

Metabolic syndrome defines a state of metabolic dysregulation characterized by insulin resistance and a predisposition to type 2 diabetes, central and visceral obesity, hypertension and dyslipidemia. The metabolic dysregulation can be caused by an underlying endocrine imbalance mediated by the adrenal steroids aldosterone and cortisol as reported by Kidamby et al. Hypertension 2007; 49:704-711.

Hypercortisolemia refers to conditions that are characterized by high levels of circulating cortisol. High levels of plasma cortisol may directly contribute to a pathological condition, represent a sign of a pathological condition or be of non-pathological nature.

In one preferred embodiment, the present invention provides the Combination of the Invention for use in the treatment of Cushing's syndrome. The Combination of the Invention sustains the cortisol reduction effect of Compound A. Without being bound or limited by the theory, it is understood that somatostatin analogue, particularly pasireotide, improves or maintains the effect of Compound A by targeting ACTH. Thus in one preferred embodiment, Cushing's syndrome is ACTH-dependent Cushing's syndrome, preferably Cushing's disease.

In addition to elevated ACTH level due to ACTH-secreting pituitary tumor, other tissues, for instance, tumors outside the normal pituitary-adrenal system, such as small cell lung cancer, can produce ACTH that affects the adrenal glands. Thus in one embodiment the patient having Cushing's syndrome has elevated level of ACTH of non-pituitary origin.

On the other hand the present invention also envisages improved treatment of Cushing's syndrome in which the hypercortisolism is ACTH independent. Without being bound or limited by the theory, pasireotide reduces the level of ACTH whose increase could be potentially caused due to the administration of Compound A.

In one aspect, the present invention provides Compound A for use in combination of a somatostatin analogue, preferably pasireotide, for treating Cushing's syndrome.

In one aspect, the present invention provides a method of treating Cushing's syndrome comprising administering (1) Compound A and (2) a somatostatin analogue to a patient simultaneously, separately or sequentially.

In one aspect the present invention provides a use of the Combination of the Invention for the manufacture of a medicament for the treatment of Cushing's syndrome.

In one aspect the present invention provides a use of Compound A in free form, complex form or in the form of a pharmaceutically acceptable salt, for the preparation of a medicament to be used in combination with a somatostatin analogue.

In one aspect the present invention provides a commercial package comprising the Combination of the Invention, together with instructions for simultaneous, separate or sequential use thereof in the treatment of Cushing syndrome.

Preferably said somatostatin analogue is pasireotide.

EXAMPLES

The following examples illustrate the invention described above, but are not, however, intended to limit the scope of the invention in any way. Other test models known as such to the person skilled in the pertinent art can also determine the beneficial effects of the invention.

Example 1

Phosphate Salt of 4-(R)-6,7-dihydro-5H-pyrrolo[1,2-c]imidazol-5-yl-3-fluoro-benzonitrile (Form A)

2 g of free base was dissolved in a 40 ml ethanol and 1 equivalent phosphoric acid was added over the course of several minutes. After addition, solids were collected by filtration. The solids were dried at 22° C. under nitrogen flow. About 1.8 g were collected.

The molar ratio of phosphate to 4-(R)-6,7-dihydro-5H-pyrrolo[1,2-c]imidazol-5-yl-3-fluoro-benzonitrile in the obtained salt is 1:1.

In water, the phosphate salt was soluble at the 0.1% target concentration and stable for 2 days at 50° C. The free base remained largely insoluble. It converted from a free flowing solid into an oily material within a short time after contact with water, and remained as such for the 2 day period at 50° C.

Hygroscopicity

Sorption/desorption isotherms were measured using the VTI 100 humidity microbalance (VTI Corporation, Hialeah, Fla., USA). Measurements were carried out at 25° C. Samples were dried under $N_2$ flow at 25° C.

The hygroscopicity of the phosphate salt was found to be only 0% water uptake at 5% RH and 0.9% water uptake at 75% relative humidity.

Excess solids were equilibrated in each solvent for over 24 hours at 25° C.±0.1. Concentration in supernatant was measured by gravimetry for organic solvents and by HPLC from aqueous solvents and propylene glycol.

The following results were obtained for the phosphate salt in comparison with the free base:

TABLE 1-1

| Solubility profile (mg/ml) | | |
|---|---|---|
| Solvent | Free base | Phosphate salt |
| pH 1 | >50 | >50 |
| pH 6.8 | 28.6 | >50 |
| Water | 7.2 | >50 |
| Ethanol | >50 | 5.8 |
| Acetone | >50 | 1.5 |
| Propylene glycol | 34.4 | 1.5 |
| Ethyl Acetate | >50 | n.d. |

This shows that the solubility of the phosphate salt is comparably low in non-aqueous solvents which are thus anti-solvents for the salt, thus making it possible to achieve good precipitation and thus good yields and good purity. On the other hand, the solubility in water is better than that for the free base which is advantageous for providing oral or parenteral formulations.

The melting point was determined by TG/DTA as described above and was determined to be 210.2° C.

Example 2

Patients with Cushing's disease achieve normal urinary cortisol with Compound A, a potent 11β-hydroxylase inhibitor: preliminary results from a multicenter, proof-of-concept study Introduction:

The clinical features and complications of Cushing's syndrome result from chronic excess of circulating cortisol, typically quantified by 24-hour urinary free cortisol (UFC). COMPOUND A is a potent inhibitor of 11β-hydroxylase. Since 11β-hydroxylase catalyzes the final step of cortisol synthesis, COMPOUND A is a potential new treatment for all forms of Cushing's syndrome.

Methods:

Adult patients with mild-to-severe Cushing's disease (UFC>1.5× the upper limit of normal [ULN], mean of three collections in 14 days) received oral COMPOUND A for 10 weeks in an open-label study. COMPOUND A was initiated at 2 mg bid. Dose escalation was planned every 2 weeks to 5, 10, 20 and 50 mg bid until UFC normalized, in which case the dose was maintained until day 70, when treatment stopped. Dose reduction for tolerability was permitted. UFC was assessed on the penultimate day of each 2-week period. Patients were monitored until day 84. The primary endpoint was UFC≤ULN or a ≥50% decrease from baseline at day 70 using the mean of 3 UFC samples collected during the week before day 70.

Figure 1:
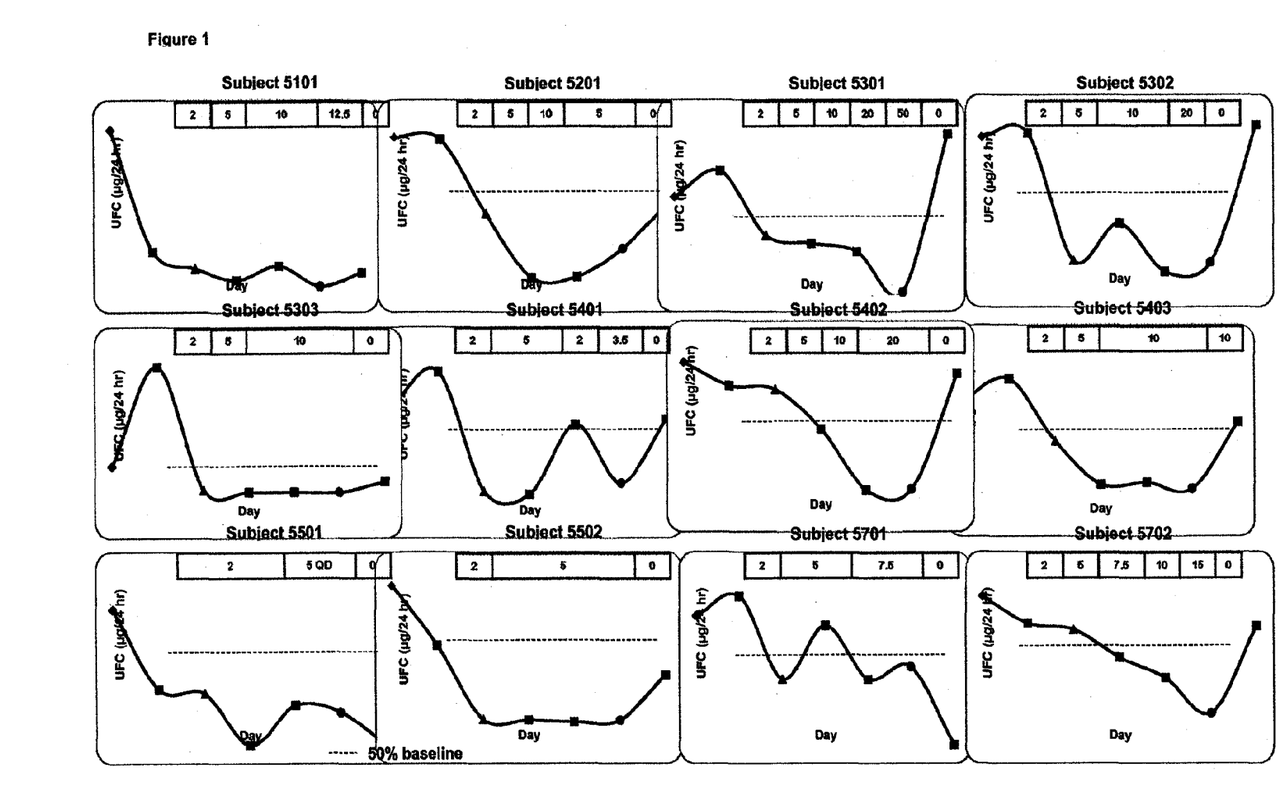
FIG. 1 illustrated the urinary free cortisol (UFC) levels over time for patients treated with Compound A.
Figure 2:
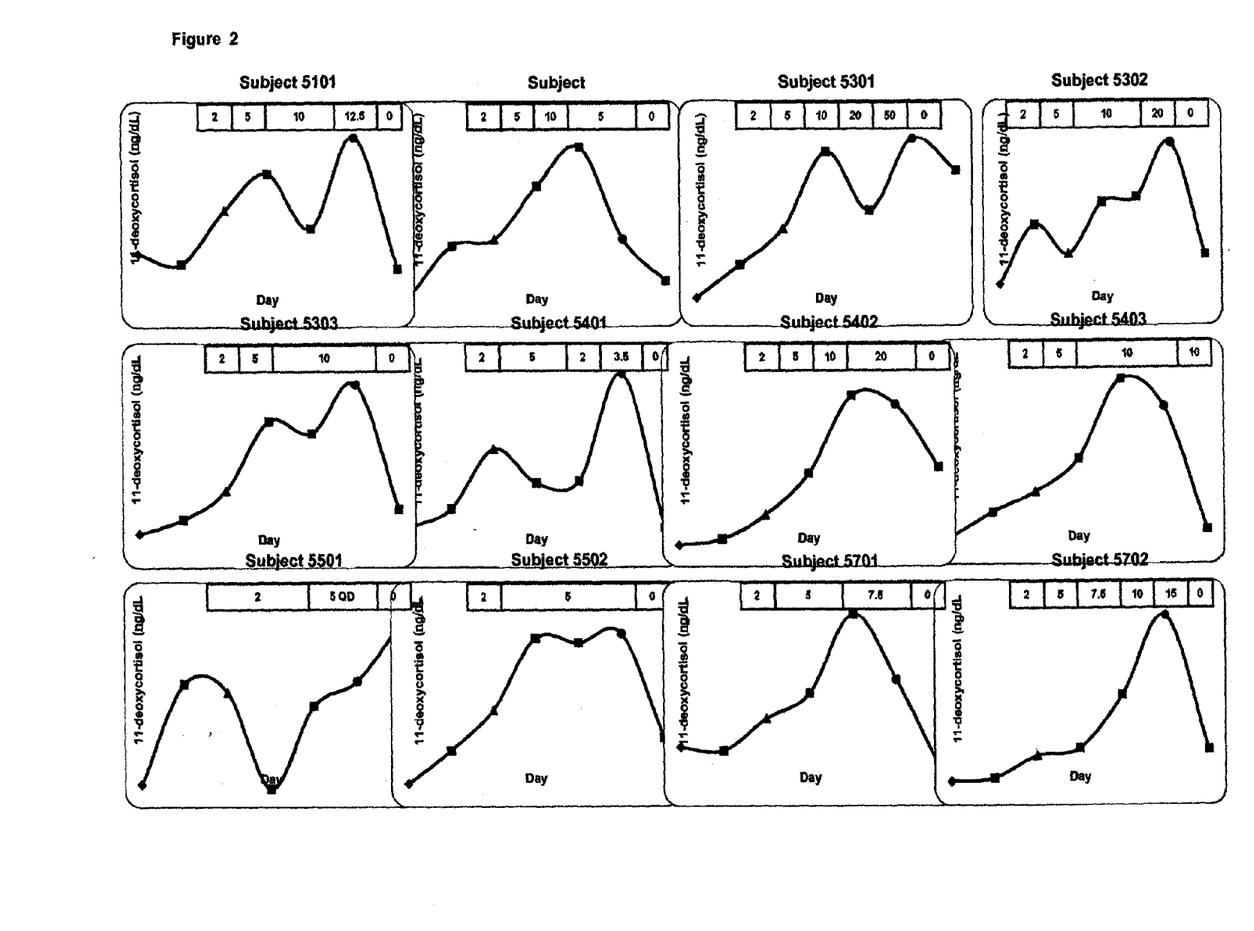
FIG. 2 illustrates the deoxycortisol levels over time for patients treated with Compound A.
Figure 3:
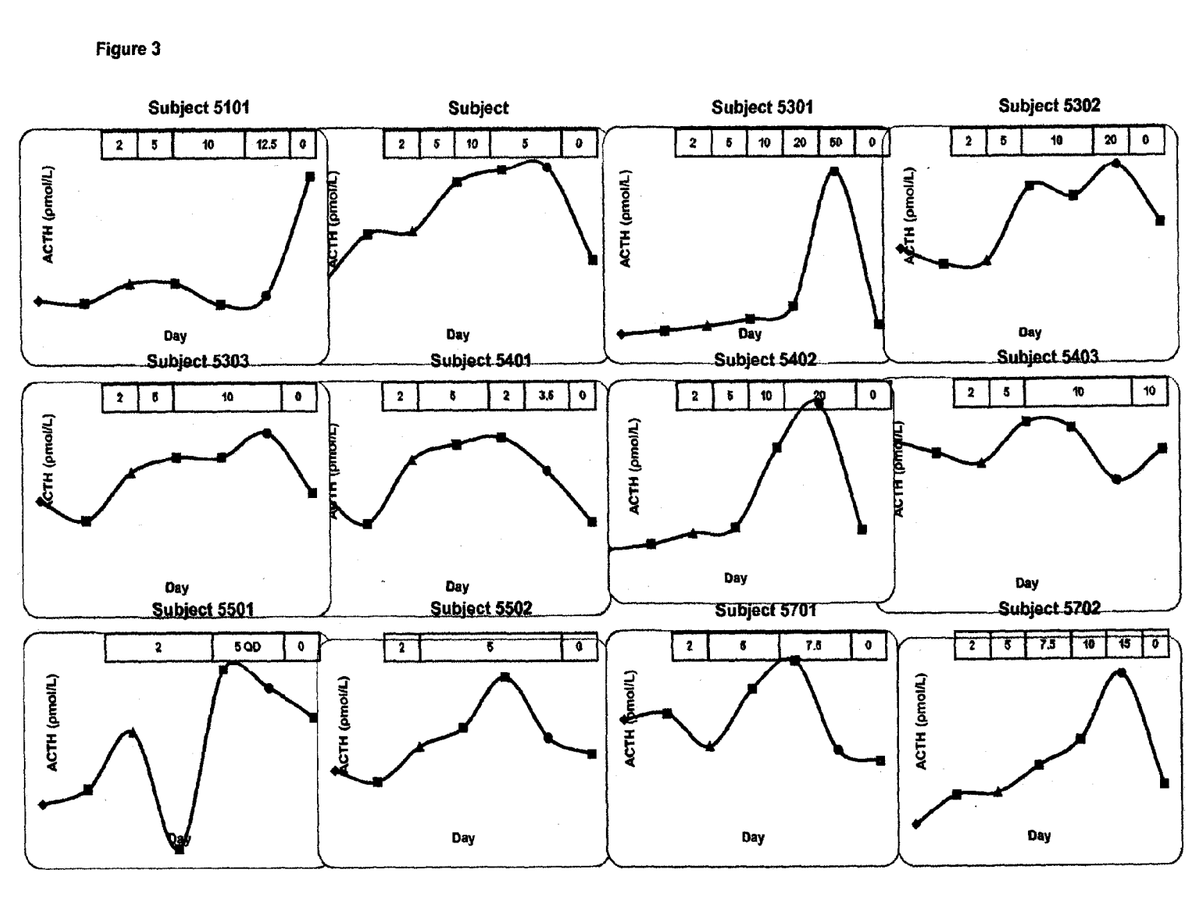
FIG. 3 illustrates the ACTH levels over time for patients treated with Compound A.

Results:

Twelve patients (aged 25-55 years; 4 men) have been enrolled and 9 have completed the study to date. Their UFC, deoxycortisol, ACTH level were individually shown in the FIGURES. Nine patients had prior surgery. Baseline UFC range was 1.6-17.0×ULN (Mean UFC±SD, μg/24 h, 346±385; range 115-153). UFC levels were normal on at least one assessment in 11 of 11 patients during the study. The primary endpoint was achieved by all 9 patients who have completed the active treatment phase, 8 of whom had normal UFC levels on day 70. After treatment discontinuation, UFC was >ULN in 6 patients with measurements at day 84. The median dose of COMPOUND A associated with UFC normalization was between 5 and 10 mg bid. At day 70, mean SBP decreased by 13.1 mmHg from baseline. COMPOUND A was generally well tolerated; the most frequently reported adverse events were fatigue (7/12), nausea (4/12) and headache (3/12). Five patients experienced ACTH levels>2× baseline. Four patients experienced study drug-related hypokalemia ($K^+$<3.5 mmol/L; min 3.1 mmol/L). There were no serious AEs of suspected drug relationship.

Conclusion:

Compound A demonstrated efficacy with a satisfactory safety profile in this proof-of-concept study in patients with Cushing's disease.

Example 3

Combination Study of Compound A and Pasireotide in Rats

The purposes of this nonclinical study were to determine the toxicity of COMPOUND A and SOM230 in combination.

The combination treatment included daily oral administration of COMPOUND A, and once daily subcutaneous injection of SOM230 to rats. In addition, the toxicokinetic characteristics of COMPOUND A/SOM230 were determined.

COMPOUND A, formulated in Ultrapure water, was administered by oral gavage (5 mL/kg) alone or in combination to SOM230, formulated with Acetate buffered solution pH 4.5, for injection USP, and administered by subcutaneous injection (interscapular area, 1 mL/kg) to 5 groups (10/sex/group) of Wistar Hannover rats at daily doses of 1.5/0.03, 5/0.1, 20/0.3, 20/ and /0.3 mg/kg/day COMPOUND A/SOM230. Another group of rats (10/sex) received daily doses of Ultrapure water, by oral gavage, and the Acetate buffered solution pH 4.5 for injection USP, by subcutaneous injection, and served as controls. At initiation of dosing, animals were approximately 7-8 weeks old and the males were 176 to 216 g and the females were 123 to 165 g.

Study activities included clinical examinations, involving twice daily exams for mortality and signs of ill health or reaction to treatment, daily pre-dose and 1-hour post dose cage-side observations, weekly detailed examination, body weights and food consumption, two ophthalmic examinations (pretreatment and week 13), clinical pathology (hematology, coagulation and clinical biochemistry, urinalysis) and immunology at the end of dosing (Adrenocorticotropic hormone, Corticosterone, Growth hormone, Insulin-like growth factor and urinalysis for Corticosterone). Toxicokinetic evaluations were performed on day 1, and during week 11 (0.5, 1, 3, 7 and 24 hours post dose) on groups receiving the COMPOUND A/SOM230 combination. Post mortem evaluation included macroscopic observations, organ weight assessments (absolute and relative to body) and microscopic examinations.

In-life observations: There were no COMPOUND A/SOM230 related deaths, clinical signs of toxicity, adverse effects on food consumption or ocular changes during the conduct of this study.

Effects on serum corticosterone (PD marker): COMPOUND A or SOM230 alone elicited decreases in serum corticosterone in females only. Administration of COMPOUND A/SOM230 in combination elicited moderate decreases in serum corticosterone in males and females at all dose levels tested (table 1). This data suggests that the combination of COMPOUND A and SOM230 provided better efficacy compared to either agent alone.

TABLE 1

Serum corticosterone changes in rats administered COMPOUND A/SOM230 when compared to control

| | | Dose (SOM230/COMPOUND A) | | | | | |
|---|---|---|---|---|---|---|---|
| | | 0/0 | 1.5/0.03 | 5/0.1 | 20/0.3 | 20/— | —/0.3 |
| Mean serum corticosterone level (n = 10) | Male (n = 10) | 236.23 | 170.92 | 146.44 | 177.80 | 221.83 | 233.68 |
| | Female (n = 10) | 259.50 | 167.52 | 149.53 | 176.34 | 166.76 | 190.56 |
| Change from Control (%) | Male | | −28% | −38% | −25% | —* | —* |
| | female | | −35% | −42% | −32% | −36% | −27% |

*A dash (—) indicates absence of change in group.

Effects on adrenal gland (potential target organ of toxicity): Treatment with COMPOUND A is associated with increased adrenal gland organ weights (more pronounced in females), co-treatment with SOM230 prevented the adrenal weight increase by COMPOUND A (table 2). Additionally, treatment of COMPOUND A produced adrenalcortical hypertrophy in female rats, and the co-treatment with SOM230 prevented adrenal hypertrophy by COMPOUND A in female rats. This data suggests that co-treatment with SOM230 may prevent the side effects on adrenal gland by COMPOUND A.

TABLE 2

Adrenal gland weights in male and female rats

| | | Dose (SOM230/COMPOUND A) | | | | | |
|---|---|---|---|---|---|---|---|
| | | 0/0 | 1.5/0.03 | 5/0.1 | 20/0.3 | 20/— | —/0.3 |
| Absolute adrenal weights (g) | Male (n = 10) | 0.04511 | 0.04136 | 0.03747 | 0.03617 | 0.04969 | 0.03615 |
| | Female (n = 10) | 0.05444 | 0.05809 | 0.05549 | 0.05296 | 0.07002 | 0.04585 |
| Relative adrenal weight (% of body weight) | Male (n = 10) | 0.01235 | 0.01237 | 0.01265 | 0.01271 | 0.01386 | 0.01326 |
| | Female (n = 10) | 0.02531 | 0.02649 | 0.02635 | 0.02593 | 0.02907 | 0.02432 |

In conclusion, administration of COMPOUND A/SOM230 given in combination by daily oral gavage/subcutaneous injection to rats for 13 weeks was well tolerated in life, and did not exacerbate the target organ toxicity as compared to SOM230 or COMPOUND A alone. Furthermore, the co-treatment seems to provide better efficacy as shown by more consistent reduction of serum corticosterone, and better safety as shown by reduced adverse effects on adrenal gland.

Example 4

Combination Study of Compound A and Pasireotide in Cushing's Syndrome

Study Design

Figure 4:
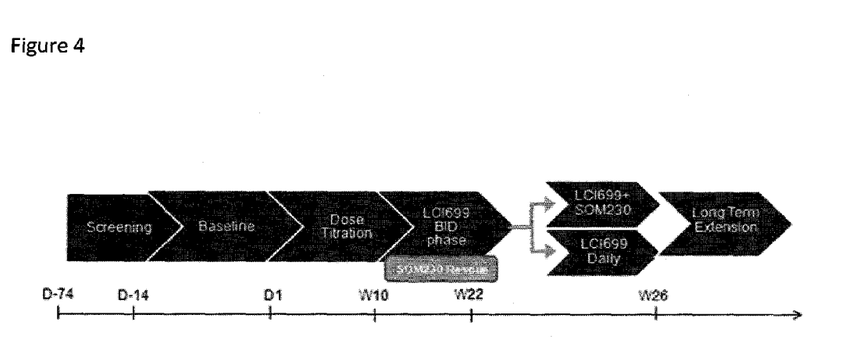
FIG. 4 summarizes the study design and dosing schedule for Combination Study of Compound A and pasireotide in Cushing's syndrome.

The study consists of a screening period of up to 60 days, a 10-14-day baseline period and a 10-week (70 days) treatment period with sequential dose escalation followed by 12 week COMPOUND A BID treatment phase where patients will continue to receive COMPOUND A at the maximally tolerated dose with the ability to enter a SOM230 Rescue Phase if needed. At week 22, patients will be assessed to determine entry into one of the two groups for 4 weeks: (1) COMPOUND A b.i.d. plus pasireotide or (2) COMPOUND A once a day dosing. The addition of pasireotide s.c. could take place earlier (between week 10 and week 22) if deemed necessary as a rescue therapy. At the end of week 26, patients on COMPOUND A daily dosing will have the option to enter a 12 month extension phase.

Note: Patients with baseline UFC>3×ULN will start at 5 mg bid (in lieu of 2 mg bid)

Population:

The study population will be comprised of male and female patients with endogenous hypercortisolism due to adrenal Cushing's syndrome (ACTH independent) or due to increased ACTH production from the pituitary (Cushing's disease) or from ectopic origin (ectopic ACTH). Patients should have either failed standard therapy (including surgery) or can be de novo patients for whom surgery is not an option.

Inclusion/Exclusion Criteria:
Inclusion:
1. Male or female patients aged 18-75 years
2. Diagnosis of Cushing's Syndrome:
   as evidenced by the following criteria:
   a. Cushing's Disease:
      UFC>1.5×ULN (Mean value of three 24-hour urine samples collected within 14 days).
      Morning plasma
      Confirmation of pituitary origin of excess ACTH by at least one of the following three:
         History of MRI confirmation of pituitary adenoma (greater than or equal to 6 mm) with positive dynamic test (e.g. CRH or high dose dexamethasone suppression test) or
         History of inferior petrosal sinus gradient>3 after CRH stimulation or
         Prior pituitary surgery with histopathology confirming an ACTH staining adenoma
   b. Adrenal Cushing's syndrome:
      UFC>1.5×ULN (Mean value of three 24-hour urine samples collected within 14 days)
      Morning plasma ACTH<the lower limit of normal, unresponsive to CRH
      Confirmation of adrenal source of hypercortisolism with at least one of the following:
         Imaging evidence of adrenal lesions compatible with ACTH-independent Cushing's syndrome or
         History of prior adrenal surgery with histopathology confirming a cortisol producing adenoma or carcinoma.
   c. Ectopic ACTH Cushing's syndrome:
      UFC>1.5×ULN (Mean value of three 24-hour urine samples collected within 14 days)
      Morning plasma ACTH≥lower limit of normal, unresponsive to CRH
      Confirmation of extra-pituitary origin of excess ACTH by at least one of the following three:
         Absent pituitary MRI image and negative CRH test together with:
            Obvious non-pituitary ACTH source (Thoracic tumor at CT and/or octreoscan), pathologically confirmed tumor of any localization OR
            Inferior petrosal sinus gradient≤3 after CRH stimulation OR
            Prior extra-pituitary surgery with histopathology confirming an ACTH staining adenoma/carcinoma 3. For patients on the following medical treatments, washout periods must be completed before baseline efficacy assessments are performed as follows:
   Inhibitors of steroidogenesis (ketoconazole, metyrapone): 1 week
   Dopamine agonists (bromocriptine, cabergoline), PPAR-gamma agonists (rosiglitazone or pioglitazone): 4 weeks
   Octreotide LAR, Pasireotide LAR and Lanreotide autogel: 8 weeks
   Mifepristone, Lanreotide SR: 4 weeks
   Octreotide and Pasireotide (immediate release formulation): 1 week
   Other experimental therapy: at least 5 half-lives Exclusion:
1. Use of other investigational drugs at the time of enrollment
2. History of hypersensitivity to any of the study drugs or to drugs of similar chemical classes.
3. History of malignancy of any organ system (other than localized basal cell carcinoma of the skin and other than those related to Cushing's syndrome, e.g. adrenal carcinoma or carcinoid tumors/carcinomas secreting ACTH), treated or untreated, within the past 5 years, regardless of whether there is evidence of local recurrence or metastases.
4. Pregnant or nursing (lactating) women
5. Women of child-bearing potential
6. Fertile males UNLESS the subject agrees to comply with two effective contraceptive methods for the entire duration of the study
7. Patients who have been treated with mitotane during the last 6 months prior to Visit 1
8. Patients with compression of the optic chiasm, in order to exclude patients with a tumor causing chiasmal compression requiring surgery.
9. Patients with pseudo-Cushing's syndrome [for patients with a mean UFC<3×ULN further testing to rule out this condition will be required unless Cushing's disease or ectopic or adrenal source is confirmed by histopathology]. At least 2 of 3 tests should be abnormal in order to exclude pseudo-Cushing's: low-dose dexamethasone suppression test, dexamethasone-CRH test or late-night salivary or serum cortisol.
10. Patients with renal impairment (estimated creatinine clearance<60 mL/min by the MDRD formula), serum creatinine>2.0×ULN.
11. Patients who are not biochemically euthyroid.
12. Patients who have undergone major surgery within 1 month prior to screening.
13. Diabetic patients with poorly controlled diabetes as evidenced by HbA1C>9%
14. Patients who have congestive heart failure (NYHA Class III or IV), unstable angina, sustained ventricular tachycardia, clinically significant bradycardia, advanced heart block, history of acute MI less than one year prior to study entry or clinically significant impairment in cardiovascular function.
15. Patients with liver disease such as cirrhosis, chronic active hepatitis, or chronic persistent hepatitis, or patients with ALT/AST more than 3×ULN, serum bilirubin>2.0×ULN.

If any of the following exclusions for pasireotide are met, the patient can not use pasireotide.
1. Diabetic patients with poor glycemic control as evidenced by HbA1c>8%
2. Patients with risk factors for torsade de pointes, i.e. patients with a QTcF>470 ms, hypokalemia, hypomagnesemia, uncontrolled hypothyroidism, family history of long QT syndrome, or concomitant medications known to prolong QT interval
3. Patients with history of liver disease such as cirrhosis, chronic active hepatitis B and C, or patients with ALT or AST>2×ULN, or a total bilirubin>1.5×ULN
4. Presence of Hepatitis B surface antigen (HbsAg)
5. Presence of Hepatitis C antibody (anti-HCV)
6. Known gallbladder or bile duct disease, acute or chronic pancreatitis
7. Adrenal Cushing's syndrome or Ectopic ACTH Cushing's Syndrome patients Investigational and Reference Therapy:

Study will start with newly enrolled patients on either 2 mg bid of COMPOUND A if baseline mUFC is ≤3×ULN or 5 mg bid if baseline mUFC is >3×ULN and they will increase their dose every 2 weeks until week 10. All patients will continue COMPOUND A b.i.d. monotherapy from week up to week 22. Pasireotide 300 μg b.i.d. s.c. will be potentially administered as an add-on therapy (Week 22-26) or if needed sooner (Week 10-22) as rescue therapy. Patients that do not receive pasireotide at week 22 or earlier may be potentially administered COMPOUND A in a once daily dose (q.d.) instead of b.i.d. for 4 weeks Efficacy/Pharmacodynamic Assessments:

Efficacy assessments will include urinary free cortisol, plasma ACTH, cortisol, 11-deoxycortisol and renin, plasma and urine deoxycorticosterone, plasma and urine aldosterone, serum and urine sodium and potassium, salivary cortisol and aldosterone, testosterone and estradiol, LH, FSH, IGF-1, TSH, free T4, HbA1c and plasma insulin.

Data Analysis:

The primary variable is defined as the proportion of responders to COMPOUND A. A patient is considered to be a responder if the mean UFC level from the Week 10 24-hour urine samples is ≤ULN or represents a ≥50% decrease from baseline. Patients who discontinue for a disease or treatment related reason (e.g. death, adverse event, clinical disease progression etc.), or whose mean Week 10 24-hour UFC levels are higher than the normal limit and whose decrease in UFC is <50%, are classified as non-responders. Patients who have <2 baseline or post-baseline 24-hour UFC measurement will not be included in the primary analyses.

The proportion of responders and the associated 95% confidence interval will be estimated using the Exact Binomial Test.

The primary efficacy variable is defined as the proportion of responders to COMPOUND A monotherapy at week 22. A patient needing rescue therapy prior to week 22 will also be classified as a non-responder.

Responders will be classified further into patients with controlled UFC and partially controlled UFC.

The invention claimed is:

1. A combination of (a) Compound A (R)-4-(6,7-Dihydro-5H-pyrrolo[1,2-c]imidazol-5-yl)-3-fluoro-benzonitrile; and (b) a somatostatin analogue, wherein (a) and (b) are present in each case in free form, complex form or in the form of a pharmaceutically acceptable salt.

2. The combination of claim 1, wherein said somatostatin analogue is octreotide, pasireotide or lanreotide.

3. The combination of claim 2, wherein said somatostatin analogue is pasireotide.

4. The combination of claim 1 for simultaneous, separate or sequential use.

5. The combination of claim 1 being a fixed combination.

6. The combination of claim 5 further comprises a pharmaceutically acceptable carrier.

7. The combination of claim 1 being a non-fixed combination.

8. A method of treating Cushing's syndrome, comprising administering (1) Compound A (R)-4-(6,7-Dihydro-5H-pyrrolo[1,2-c]imidazol-5-yl)-3-fluoro-benzonitrile and (2) a somatostatin analogue to a patient simultaneously, separately or sequentially.

9. The method of claim 8, wherein said somatostatin analogue is octreotide, pasireotide or lanreotide.

10. A commercial package comprising a combination according to claim 1, together with instructions for the method of treating Cushing syndrome, wherein said combination is administered simultaneously, separately or sequentially.

11. A method according to claim 8 wherein said Cushing's syndrome is Cushing's disease.

12. A commercial package according to claim 10 wherein said Cushing's syndrome is Cushing's disease.

* * * * *